US011641681B2

(12) United States Patent
Ming et al.

(10) Patent No.: US 11,641,681 B2
(45) Date of Patent: May 2, 2023

(54) DATA TRANSMISSION AND REMOTE ACTIVITY MONITORING

(71) Applicant: Micron Technology, Inc., Boise, ID (US)

(72) Inventors: Kristina L. Ming, Boise, ID (US); Lisa R. Copenspire-Ross, Boise, ID (US); Madison D. Drake, Boise, ID (US); Rosa M. Avila-Hernandez, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 122 days.

(21) Appl. No.: 17/189,775

(22) Filed: Mar. 2, 2021

(65) Prior Publication Data

US 2022/0287112 A1 Sep. 8, 2022

(51) Int. Cl.

| | |
|---|---|
| *H04W 76/14* | (2018.01) |
| *G08B 5/22* | (2006.01) |
| *G01K 1/14* | (2021.01) |
| *G01K 3/00* | (2006.01) |
| *H04W 88/06* | (2009.01) |

(52) U.S. Cl.
CPC ............. *H04W 76/14* (2018.02); *G01K 1/14* (2013.01); *G01K 3/005* (2013.01); *G08B 5/223* (2013.01); *H04W 88/06* (2013.01)

(58) Field of Classification Search
CPC ........ H04W 76/14; H04W 88/06; G01K 1/14; G01K 3/005; G08B 5/223

USPC ..................................................... 455/426.1
See application file for complete search history.

(56) References Cited

U.S. PATENT DOCUMENTS

| | | | |
|---|---|---|---|
| 9,749,740 B2 | 8/2017 | Borkhovik et al. | |
| 9,788,907 B1* | 10/2017 | Alvi ...................... | G11B 27/34 |
| 10,307,060 B2 | 6/2019 | Tran | |
| 10,917,775 B2 | 2/2021 | Miasnik et al. | |
| 2007/0171047 A1 | 7/2007 | Goodman et al. | |
| 2012/0290311 A1 | 11/2012 | Tara et al. | |
| 2013/0057696 A1* | 3/2013 | Felt ........................ | H04N 7/186 |
| | | | 348/158 |
| 2015/0281659 A1* | 10/2015 | Hood .................... | A61G 7/0509 |
| | | | 348/143 |

(Continued)

*Primary Examiner* — Tanmay K Shah
(74) *Attorney, Agent, or Firm* — Brooks, Cameron & Huebsch, PLLC (57) ABSTRACT

Methods, apparatuses, and non-transitory machine-readable media associated with data transmission are described. Data transmission and remote activity monitoring can include detecting a triggering event and determining an output data type associated with the triggering event, wherein the output data type is a first type for display at a second device or a second type to initiate communication between the first device and one or more second devices. Data transmission can include transmitting the output data to the second device via a device-to-device data link in response to determining the output data type comprises the first type. In response to determining the output data type comprises the second type, data transmission can include initiating a two-way communication path with the second device, the two-way communication path comprising a device-to-device data link or a data link with a base station or access point and transmitting the output data to the second device.

20 Claims, 6 Drawing Sheets

(56) References Cited

U.S. PATENT DOCUMENTS

| | | | | |
|---|---|---|---|---|
| 2015/0351698 A1* | 12/2015 | Cronin | ................... | G16Z 99/00 |
| | | | | 600/595 |
| 2017/0337738 A1* | 11/2017 | Kepner | ................... | G06T 17/05 |
| 2018/0064209 A1 | 3/2018 | Hamill | | |
| 2018/0150256 A1* | 5/2018 | Kumar | ................ | G06F 13/4022 |
| 2022/0086690 A1* | 3/2022 | Iyer | ........................ | H04L 47/24 |
| 2022/0198902 A1* | 6/2022 | Yao | ........................ | G06F 9/542 |

\* cited by examiner

DATA TRANSMISSION AND REMOTE ACTIVITY MONITORING

TECHNICAL FIELD

The present disclosure relates generally to apparatuses, non-transitory machine-readable media, and methods associated with data transmission and remote activity monitoring.

BACKGROUND

Telecommunication includes any transmission, emission or reception of signs, signals, writings, images and sounds or intelligence of any nature by wire, radio, optical or other electromagnetic systems. Transmission media in telecommunication has evolved through numerous stages of technology.

Transmission paths may be divided into communication channels, which allow multiplexing multiple concurrent communication sessions.

Telecommunication media can facilitate tracking of a mobile device including identifying the location of the mobile device, whether stationary or moving. Localization can include the use of multilateration of radio signals between cell towers of a network and the mobile device or the Global Positioning System (GPS). To locate a mobile device using multilateration of mobile radio signals, an idle signal is emitted to contact nearby antenna towers. Mobile positioning may be used for location-based services that disclose coordinates of a mobile device. This can be used to approximate the location of a mobile device, and thereby also its user.

DETAILED DESCRIPTION

Systems, machine-readable media, and methods related to data transmission are described. Mobile devices (e.g., tablets, smartphones, smart watches, GPS devices, laptops, etc.) offer tracking of the device, but may not allow for real-time information to be transmitted, for instance, between the mobile device and an observer device. In addition, tracking devices such as those utilizing radio frequency identification (RFID) may be limited to in-home tracking.

Examples of the present disclosure can leverage low-latency, high-bandwidth networks (e.g., 5G networks, fast wireless communication, etc.) that include wireless receivers, transmitters, etc. to allow for two or more device (e.g., a wearable device and an observer device) to communicate using the aforementioned networks for everyday and emergency situations. Such examples can include a wearable device (e.g., a wearable mobile device that may include sensors and an observer device that gives a third party the ability to communicate with the wearer of the wearable device and control aspects of the wearable device worn by a person being monitored.

Examples of the present disclosure can include a method for data transmission including detecting, at a first processing resource of a first device, a triggering event and determining, at the first processing resource, an output data type associated with the triggering event, wherein the output data type is a first type for display at a second device or a second type to initiate communication between the first device and one or more second devices.

The method can include transmitting, via a radio, the output data to a second processing resource of the second device via a device-to-device data link in response to determining the output data type comprises the first type for display at the second device. The method can include, in response to determining the output data type comprises the second type to initiate communication between the first device and one or more second devices, initiating a two-way communication path with the second processing resource of a second device, the two-way communication path comprising a device-to-device data link or a data link with a base station or access point. The method can include transmitting, via the radio and the one-way communication path, the two-way communication path, or both, the output data to the second processing resource of the second device.

In the following detailed description of the present disclosure, reference is made to the accompanying drawings that form a part hereof, and in which is shown by way of illustration how one or more embodiments of the disclosure can be practiced. These embodiments are described in sufficient detail to enable those of ordinary skill in the art to practice the embodiments of this disclosure, and it is to be understood that other embodiments can be utilized and that process, electrical, and structural changes can be made without departing from the scope of the present disclosure.

It is also to be understood that the terminology used herein is for the purpose of describing particular embodiments only and is not intended to be limiting. As used herein, the singular forms "a," "an," and "the" can include both singular and plural referents, unless the context clearly dictates otherwise. In addition, "a number of," "at least one," and "one or more" (e.g., a number of memory devices) can refer to one or more memory devices, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled," and "coupling" mean to be directly or indirectly connected physically or for access to and movement (transmission) of commands and/or data, as appropriate to the context.

The figures herein follow a numbering convention in which the first digit or digits correspond to the figure number and the remaining digits identify an element or component in the figure. Similar elements or components between different figures can be identified by the use of similar digits. For example, 100 can reference element "00" in FIG. 1, and a similar element can be referenced as 200 in FIG. 2. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

Figure 1:
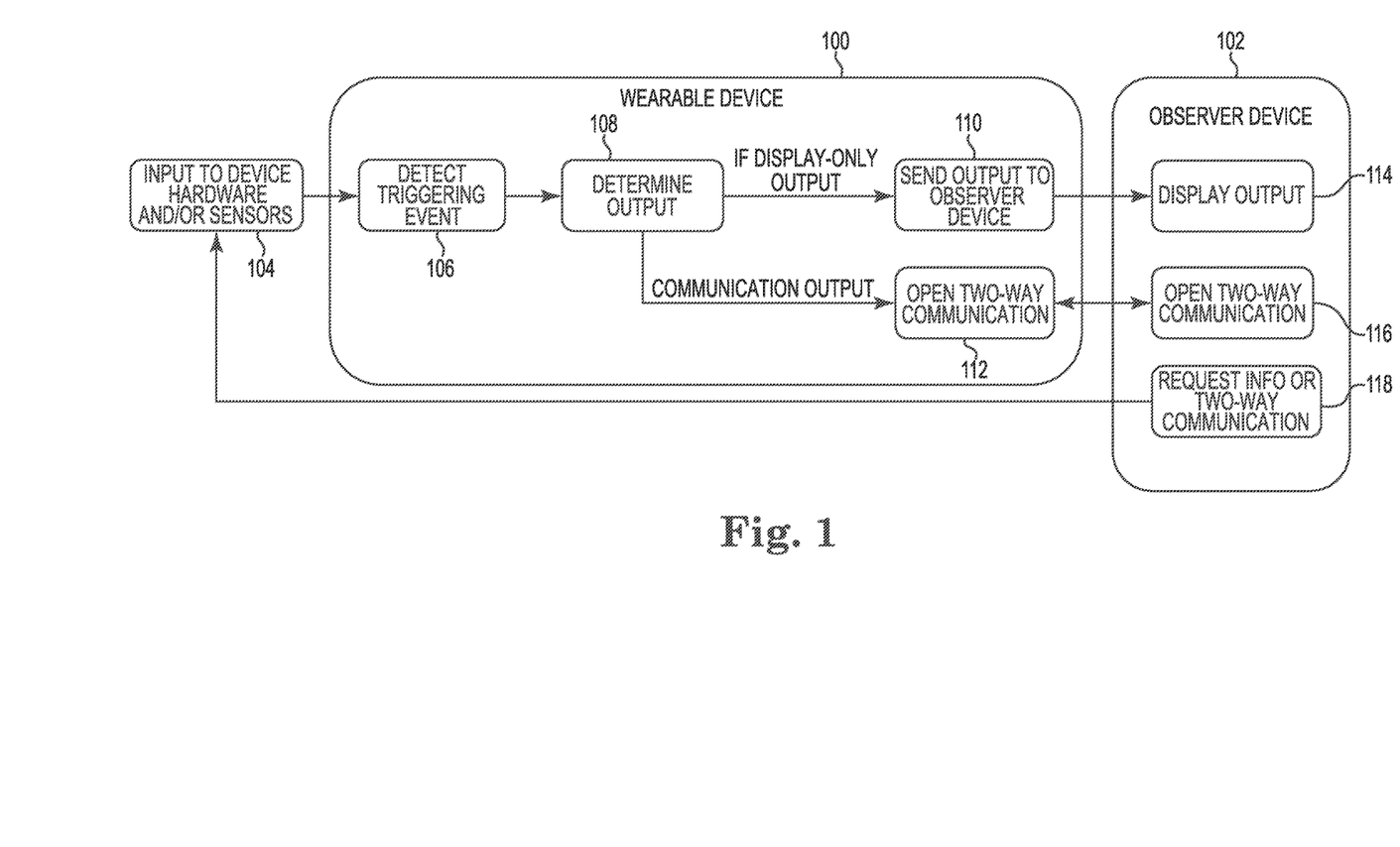
FIG. 1 is a functional diagram representing a system for data transmission in accordance with a number of embodiments of the present disclosure.

FIG. 1 is a functional diagram representing a system for data transmission in accordance with a number of embodiments of the present disclosure. FIG. 1 illustrates a wearable device 100 in communication with an observer device 102. While one observer device 102 is illustrated in FIG. 1, more than one observer device 102 may be in communication with the wearable device 100. Wearable device 100 can include, for instance, a device that can be worn by a user and has the ability to communicate with the observer device 102. For instance, the wearable device 100 may include a wearable monitor, a smart watch, or other device that can communicate using a low-latency, high-bandwidth network such as 5G. Put another way, the wearable device 100 can include a receiver and/or a transmitter that enables faster and larger capacity wireless connections. The wearable device 100 may or may not be linked to a separate mobile device (e.g., a smartphone) to enable communications. In some examples, the wearable device 100 may communicate with the observer device 102 via a two-way communication path comprising a device-to-device data link or a data link with a base station or access point.

The observer device 102 may be a mobile device or stationary device that an authorized user can use to observe a wearer of the wearable device 100. For example, a dementia patient may wear the wearable device 100, and the patient's child or children may be authorized users having access to an observer device 102 or devices. For instance, an observer device or devices 102 may be tablets, smartphones, or other devices that can communicate with the wearable device using a low-latency, high-bandwidth network such as 5G.

The wearable device 100, in some examples, may be in communication with a sensor or sensors. For instance, sensors may include health sensors (e.g., biometric sensor such as a heart monitor, blood glucose monitor, kidney function monitor, lung function monitor, oxygen monitor, etc.), temperature sensors (e.g., body temperature, ambient temperature, etc.), location sensors (e.g., GPS or other location monitor), or battery sensors, among others. The wearable device 100 may also include a timer, clock, camera, microphone, speaker, battery, or other hardware. In some examples, the sensors and/or other hardware may be configurable at the wearable device 100 or via the observer device 102. For instance, an authorized user may configure a health sensor to alert the wearable device 100 if a threshold health event occurs (e.g., blood pressure above a threshold, blood glucose levels above a threshold, etc.). In another example, a battery sensor may be configured to notify the wearable device when the battery falls below a threshold charged level. The configuration can be performed via the wearable device 100, the observer device 102, or both.

At 104, the wearable device 100 can receive input to its hardware (e.g., a processing resource) and/or associated sensors. For instance, the wearable device 100 may receive location information from a location sensor, an attempted communication from the observer device 102 at a low latency, high bandwidth wireless receiver, a temperature reading at a temperature sensor, etc. At 106, the wearable device can detect (e.g., at a processing resource) a triggering event. A triggering event can include an event that triggers an output to an observer device. The triggering event may include an event or signaling associated with a sensor or other hardware associated with the wearable device 100.

For instance, a triggering event may include the wearable device 100 arriving or leaving a particular location at a particular time, the wearable device 100 being located outside of an expected area (e.g., immediately or for a particular time period), the wearable device 100 being located in a same location for longer than a threshold time period (e.g., at a grocery store for 6 hours), the wearable device 100 have a battery level below a particular threshold, an ambient temperature or wearer temperature above or below a particular threshold, and/or a threshold health event.

In some examples, a triggering event may include manual inputs from a wearer of the wearable device 100, an authorized user of the observer device 102, or both. For instance, a wearer of the wearable device 100 may signal that he or she is lost, the authorized user of the observer device 102 may request information from the wearer of the wearable device 100, or either party may send a reminder or message to the other, such as a medication or appointment reminder from the observer device 102 or a reminder that the wearer is leaving for an appointment from the wearable device 100. For instance, the observer device 102 may request information or two-way communication from the wearable device 100 at 118. Such an example may include a child requesting, via the observer device 102, a status check of an elderly parent wearing the wearable device who has been running an errand for a longer than normal time.

In some examples, the triggering event can include an emergency call, for instance 118, from a known contact. For instance, a particular observer device or devices 102 may be known contacts such that they have been placed on a list as a safe contact and/or an emergency contact. Communication from a known contact may trigger particular outputs from the wearable device 100, for instance.

At 108, an output can be determined in response to the triggering event. The output, for example, can include an action to be taken in response to the triggering event. The output may be determined to be a display-only output or a communication output. For instance, a display-only output includes an output data type for display at the observer device or devices 102, for instance at 114, via a graphical user interface or other display. Put another way, display-only output may not include audible communication or two-way communication. Examples may include a notification badge on a display of a smartphone or image data (e.g., a photograph of a current location of the wearer of the wearable device 100). In some instances, the display-only output may include one-way communication (e.g., from the wearable device 100 to the observer device 102). In such an example, the wearable device 100 may only include a transmitter capable of faster wireless transmission or may also have a receiver capable of faster wireless transmission. The observer device 102 may only include a receiver capable of faster wireless transmission or may also have a transmitter capable of faster wireless transmission.

Communication output may include an output data type to initiate communication between the wearable device 100 and the observer device or devices 102. Examples may include a text message, phone call, or video call, among others. Communication output can be two-way communication, allowing for transmission from the wearable device 100 to the observer device 102 and vice versa. In such examples, both the wearable device 100 and the observer device 102 can have a wireless receiver and transmitter for low-latency, high-bandwidth wireless transmission. Communication can be initiated by the wearable device 100 (e.g., at 112), by the observer device (e.g., at 116), or both.

Example outputs by the wearable device 100 can include the wearable device 100 sending a message or alert with location information to the observer device 102. For instance, a message or alert that is display-only may be sent, for instance at 110, to notify the observer device 102 that the wearer of the wearable device has left his or her home. This may include a written message, a video without sound of the wearer leaving, a display badge, etc. Similar, a message or alert with location information may include a phone call, text message, video message, or other potential two-way communication sent to the observer device 102 for instance at 112.

Other example output data includes image data such as photographs or video and audio data. For instance, a wearer of the wearable device 100 may indicate that he or she is lost (e.g., by pushing a button on the wearable device 100). This indication may be detected as a triggering event at 106, and 108, it may be determined that initiating two-way communication at 112 with the observer device 102 is warranted. In such an example, images, video, audio, or a combination thereof may be transmitted to the observer device 102 to help the authorized user of the observer device 102 potentially locate the wearer of the wearable device 100.

Another example output data includes the initiation of two-way communication. Two-way communication may be initiated by either party, for instance as a phone call, live stream, or video call. In the previous example, a video call may allow for the authorized user of the observer device 102 to potentially locate the wearer of the wearable device 100.

In some examples, the output determined at 108 may indicate storage of particular data is warranted. For instance, if the triggering event is a threshold health event indicating a blood glucose level spike, the output data may include display-only output data (e.g., a displayed badge of the blood glucose level) sent to the observer device 102 at 110 or communication output (e.g., a text message that allows response accompanied by an audible alert of the blood glucose level) sent to the observer device 102 at 112. Upon notification, the blood glucose level may be written to a memory device of the wearable device 100, to a memory device of the observer device 102, to a cloud storage service, or any combination thereof.

In some instances, the output determined at 108 can include an automatic alert to emergency services. For instance, if the triggering event detected at 106 was a threshold health event such as a heart monitor that indicated a heart attack, the wearable device 100 may alert the observer device 102, but may also automatically, without additional human intervention, notify emergency services (e.g., contact "911").

In a similar example, the observer device 102 may receive an output from the wearable device 100 indicating the wearer of the wearable device has left an expected location (e.g., left a doctor's office without notifying the authorized user). In such an example, the observer device 102 may request communication (e.g., 118) from the wearable device 100, and if the observer device 102 is a predetermined emergency contact, the wearable device 100 may automatically answer. For instance, a parent operating the observer device 102 may contact a vulnerable adult child wearing the wearable device 100 upon notification that he or she left his doctor's appointment without contacting the parent. The contact, for instance, can include a video call that is automatically answered at the wearable device 100, so the vulnerable adult cannot ignore it.

In some examples, the output determined at 108 can include a notification with respect to a device or sensor associated with the wearable device 100. For instance, an observer device 102 and/or the wearable device 100 may be notified (e.g., audible alert, visual alert, etc.) when a battery level of the wearable device 100 falls below a threshold, or if the wearable device 100 has been left on a charger for greater than a threshold time period, which may indicate the wearer has failed to wear the wearable device 100.

Figure 2:
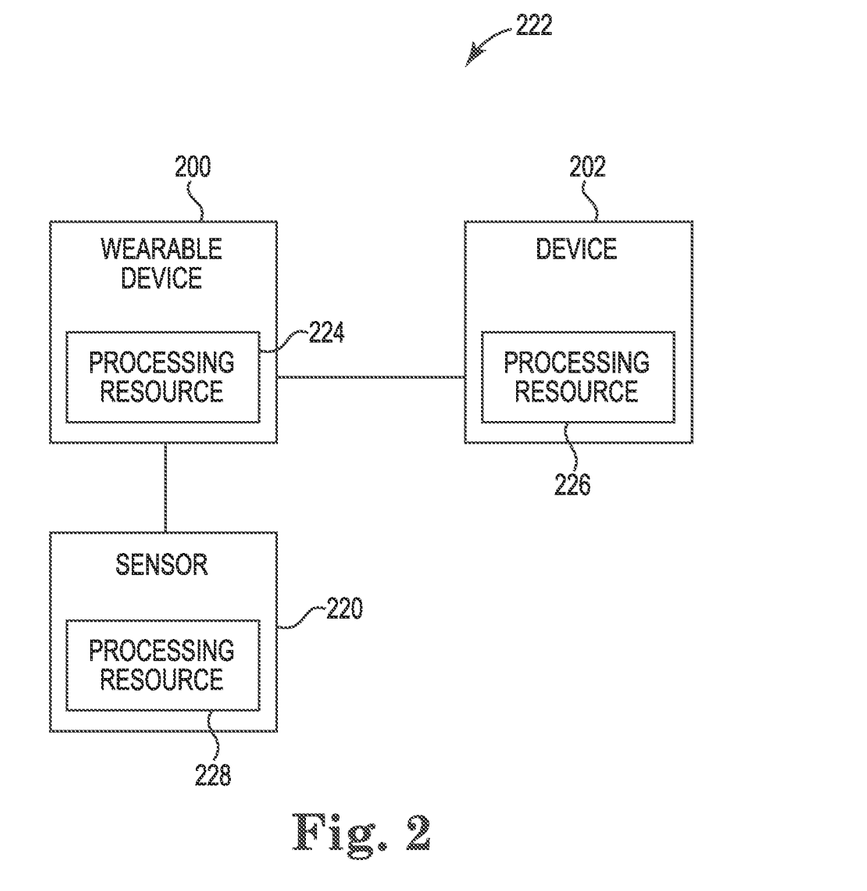
FIG. 2 is a system diagram including a wearable device, an observer device, and a sensor for data transmission in accordance with a number of embodiments of the present disclosure.

FIG. 2 is a system diagram including a wearable device 200, an observer device 202, and a sensor 220 for data transmission in accordance with a number of embodiments of the present disclosure. The system 222 can include the wearable device 200 in communication with the sensor 220 and also in communication with the observer device 202. While one wearable device 200, one observer device 202, and one sensor 228 are illustrated in FIG. 2, more of each device may be present as a part of the system 222.

The wearable device 200 can detect at the processing resource 224, a triggering event that comprises signaling received at the processing resource 224 from a processing resource 228 of the sensor 220. For example, the sensor 220, which can include at least one of a temperature sensor, a location sensor, a health sensor, a motion sensor, a battery sensor, or a combination thereof, may detect an event of importance (e.g., high blood pressure, low ambient temperature, low battery life, etc.), and signal the processing resource 224, with the signaling representing the triggering event. The wearable device 200 can determine, for instance at the processing resource 224, an output data type associated with the triggering event. Example output data types can include, for instance, a first type for display at the observer device 202 (e.g., a display-only output data type), a second type to initiate communication between the wearable device 200 and the observer device 202 (e.g., communication output data type), or both.

In a non-limiting example, the processing resource 224 of the wearable device 200 can receive input in the form of signaling from the processing resource 228 of the sensor 220. For instance, the sensor 220 may detect that a wearer of the wearable device 200 has been in a same location for longer than expected (e.g., a parent in a park for 5 hours). The processing resource 224 of the wearable device 200 can receive this signaling and determine an associated output to transmit to the observer device 202.

The observer device 202 can include a processing resource 226 in communication with the wearable device 200 via a low-latency, high-bandwidth wireless receiver, transmitter, or both. The processing resource 226 can receive at the processing resource 226, output data of the determined output data type. For instance, the wearable device 200 can initiate a one-way communication path, a two-way communication path, or both, with the processing resource 226 of the observer device 202 based on the determined output data type.

In the aforementioned example, it may be determined that the output data includes initiating a two-way communication path between the wearable device 200 and the observer device 202 (e.g., via text message) to alert the observer device that the wearer of the wearable device 200 has been in the park for 5 hours. In some instances, the wearable device 200 can transmit via the one-way communication path, the two-way communication path comprising a deviceto-device data link or a data link with a base station or access point, or both, the determined output data to the processing resource 226 of the observer device 202.

In some examples, the processing resource 224 of the wearable device 200 can automatically, with limited or no additional interaction, initiate a two-way communication path with the processing resource 226 of the observer device 202 in response to the observer device 202 initiating communication with the wearable device 200 and the observer device 202 identified as a known contact. For instance, in the aforementioned example, an authorized user of the observer device 202 may choose to contact the wearer of the wearable device 200 in response to receiving the text message regarding the length of time in the park. In such an example, if the observer device 202 has been set as a known or emergency contact (e.g., via an application or other settings), the observer device 202 can respond to the wearable device 200 will automatically initiate a two-way communication path. Put another way, if the observer device 202 is a known or emergency contact, a phone call, video message, etc. to the wearable device 200 is automatically answered, such that the wearer cannot ignore or dismiss the communication.

In some examples, the wearable device 200 can include a camera, a microphone, or both and a memory resource in communication with the processing resource 224. The processing resource 224 can share with the processing resource 226 of the observer device 202 image data, sound data, or both, collected via the camera, the microphone, or both, and stored in the memory resource. In the aforementioned example, the wearable device 200 may transmit as output data image data, sound data, or both to the observer device 202 to aid in location of the wearer of the wearable device 200. In some instances, this image data, sound data, or other collected data may be written to a memory resource of the wearable device 200, a memory resource of the observer device 202, a cloud storage system, or a combination thereof. Put another way, the processing resource 224 of the wearable device 200 can write the first type for display at the observer device 202, the second type of output data to initiate communication, or both, to a cloud storage service or other storage.

Figure 3:
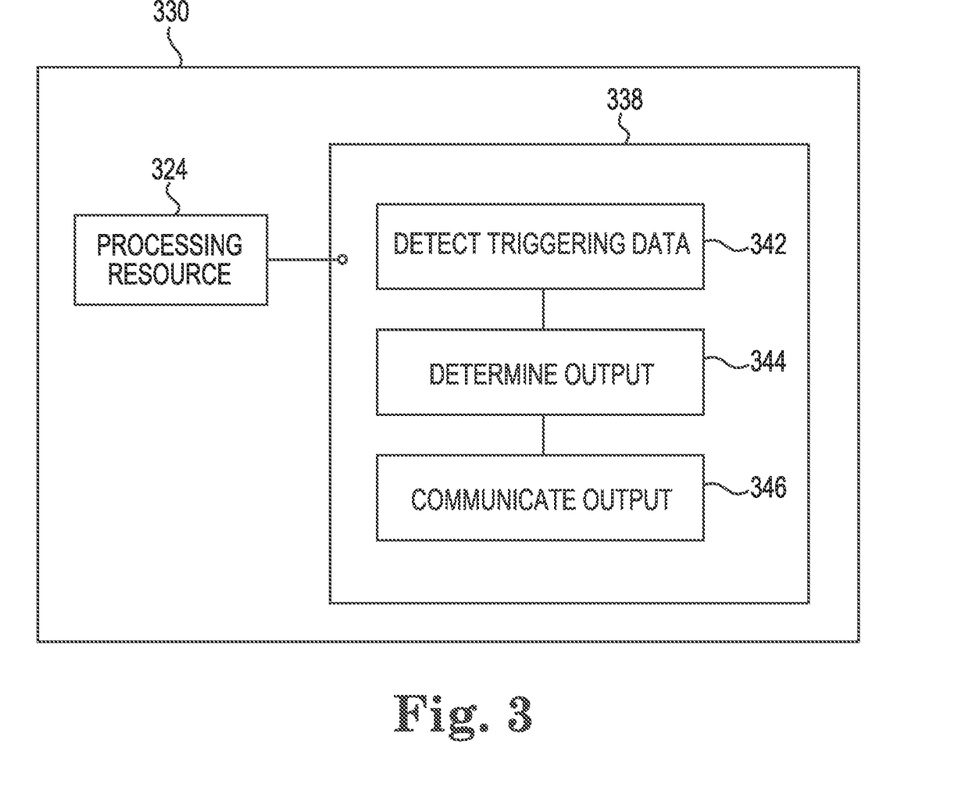
FIG. 3 is another functional diagram representing a processing resource in communication with a memory resource having instructions written thereon in accordance with a number of embodiments of the present disclosure.

FIG. 3 is another functional diagram representing a processing resource 324 in communication with a memory resource 338 having instructions 342, 344, 346 written thereon in accordance with a number of embodiments of the present disclosure. In some examples, the processing resource 324 and the memory resource 338 comprise a device or system 330 such as a wearable device (e.g., wearable device 100 or 200 illustrated in FIGS. 1 and 2, respectively).

The system 330 illustrated in FIG. 3 can be a server or a computing device (among others) and can include the processing resource 324. The system 330 can further include the memory resource 338 (e.g., a non-transitory MRM), on which may be stored instructions, such as instructions 342, 344, 346. Although the following descriptions refer to a processing resource and a memory resource, the descriptions may also apply to a system with multiple processing resources and multiple memory resources. In such examples, the instructions may be distributed (e.g., stored) across multiple memory resources and the instructions may be distributed (e.g., executed by) across multiple processing resources.

The memory resource 338 may be electronic, magnetic, optical, or other physical storage device that stores executable instructions. Thus, the memory resource 338 may be, for example, non-volatile or volatile memory. For example, non-volatile memory can provide persistent data by retaining written data when not powered, and non-volatile memory types can include NAND flash memory, NOR flash memory, read only memory (ROM), Electrically Erasable Programmable ROM (EEPROM), Erasable Programmable ROM (EPROM), and Storage Class Memory (SCM) that can include resistance variable memory, such as phase change random access memory (PCRAM), three-dimensional cross-point memory, resistive random access memory (RRAM), ferroelectric random access memory (FeRAM), magnetoresistive random access memory (MRAM), and programmable conductive memory, among other types of memory. Volatile memory can require power to maintain its data and can include random-access memory (RAM), dynamic random-access memory (DRAM), and static random-access memory (SRAM), among others.

In some examples, the memory resource 338 is a non-transitory MRM comprising Random Access Memory (RAM), an Electrically-Erasable Programmable ROM (EEPROM), a storage drive, an optical disc, and the like. The memory resource 338 may be disposed within a controller and/or computing device. In this example, the executable instructions 342, 344, 346, 348, 350 can be "installed" on the device. Additionally, and/or alternatively, the memory resource 338 can be a portable, external or remote storage medium, for example, that allows the system to download the instructions 342, 344, 346, 348, 350 from the portable/external/remote storage medium. In this situation, the executable instructions may be part of an "installation package". As described herein, the memory resource 338 can be encoded with executable instructions for data transmission.

The instructions 342, when executed by a processing resource such as the processing resource 324 can include instructions to detect triggering data. For instance, this can include signaling received from sensors such as triggering events including threshold health events, location changes, etc. In some examples, detecting triggering data can include receiving communication from a different device (e.g., an observer device) requesting information or two-way communication.

The instructions 344, when executed by a processing resource such as the processing resource 324, can include instructions to determine an output type. For instance, based on the triggering event, a determination can be made with respect to how to communicate output data to a different device or alert the device 330, itself. For instance, a low battery triggering event associated with a battery of the device 330 may indicate transmitting display-only output data to a different device and an audible and visual alert to the device 330 itself (e.g., via a speaker of the device 330).

The instructions 346, when executed by a processing resource such as the processing resource 324, can include instructions to communicate the output data. For instance, in the aforementioned example, the display-only output data can be transmitted to a display of a different device. If, for instance, communication output is determined, a two-way communication path can be initiated with the different device, and the two-way communication path can include a device-to-device data link or a data link with a base station or access point.

Figure 4:
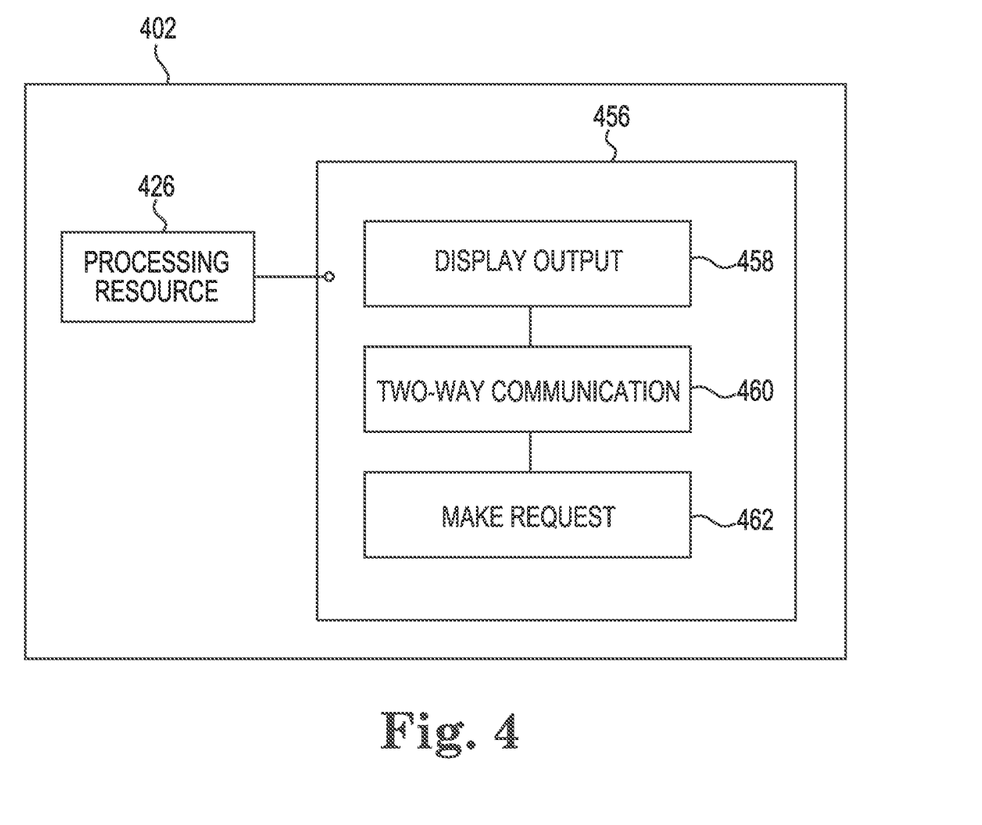
FIG. 4 is yet another functional diagram representing a processing resource in communication with a memory resource having instructions written thereon in accordance with a number of embodiments of the present disclosure.

FIG. 4 is yet another functional diagram representing a processing resource 426 in communication with a memory resource 456 having instructions 458, 560, 462 written thereon in accordance with a number of embodiments of the present disclosure. In some examples, the processing resource 426 and the memory resource 456 comprise a device or system 402 such as an observer device (e.g., observer device 102 or 202 illustrated in FIGS. 1 and 2, respectively). In some examples, the processing resource 426 and the memory resource 456 may function similarly to or analogously to processing resource 324 and memory resource 338, respectively, as described with respect to FIG. 3.

The instructions 458, when executed by a processing resource such as the processing resource 426, can include instructions to display output received from a wearable device. For instance, the device 402 may receive display-only output data from a wearable device, and can display the output, for instance as a display badge, image data, or other display-only content. In such an example, the device 402 may not be able to initiate communication with a wearable device. In such an example, the device 402 may include a via a low-latency, high-bandwidth wireless receiver.

The instructions 460, when executed by a processing resource such as the processing resource 426, can include instructions to opening or initiating two-way communication with a wearable device. For instance, the device 402 may respond, via a two-way communication path, to a wearable device and/or may initiate communication. For instance, the instructions 462, when executed by a processing resource such as the processing resource 426, can include instructions to make a request to the wearable device. In such an example, the device 402 may request information or two-way communication from the wearable device. A non-limiting example may include the device 402 requesting two-way communication with a wearable device upon receipt of a display-only output indicating the wearable device is near or has bypassed a particular ambient temperature.

In some examples, the memory resource 456 can include instructions that when executed by a processing resource such as processing resource 426 can configure an associated wearable device or sensor associated with the wearable device. For instance, the wearable device may be configured to alert the device 402 when particular triggering events are detected, and the type of alert may also be configured. In some examples, the instructions may be executable to configure particular sensors, for instance to alert the wearable device when particular thresholds are exceeded.

In a non-limiting example, a parent may have a child who communicates using sign language. The child wears a wearable device with a location sensor to monitor his or her location. The parent may receive an alert at an observer device such as device 402 that the child is outside of his or her school radius during school hours. The alert may be a display-only output or a communication output. In the former example, the parent may initiate communication with the wearable device. As a known contact, the wearable device may automatically answer the request (e.g., a video call is automatically answered). This may allow the parent to communicate with the child via sign language and help the child back to school, and/or determine why the child is outside his or her school radius. In the latter example, the parent receives output data via a two-way communication line such as a video message.

In another non-limiting example, a dog owner may have new puppy who runs away frequently. The dog wears a wearable device with a location sensor to monitor his or her location. The dog owner may receive an alert at an observer device such as device 402 that the dog is outside of the yard. The alert may be a display-only output (e.g., a display badge on the observer device, a map of the dog's location, GPS coordinates, etc.) or a communication output. In the former example, the dog owner may initiate communication with the wearable device. As a known contact, the wearable device may automatically answer the request. For instance, a call may be automatically answered, and the dog owner can talk to the dog or see via a camera of the wearable device where the dog is. The dog owner may be able to speak via a speaker of the wearable device to an adult near the dog, which may allow for easier retrieval of the dog. In the latter example, the dog owner receives output data via a two-way communication line such as a video call, so he or she can see where the dog is located.

Figure 5:
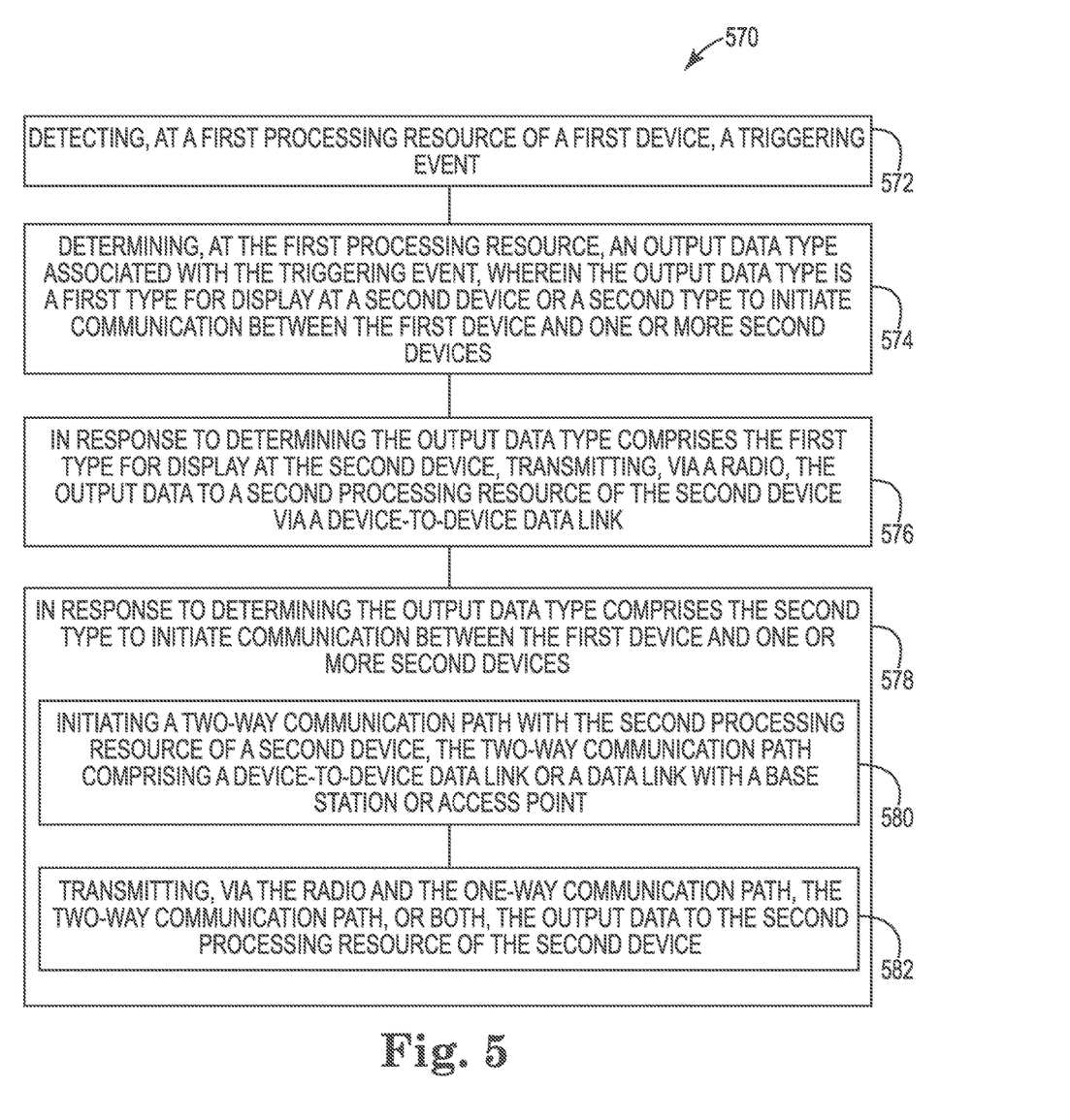
FIG. 5 is a flow diagram representing an example method for data transmission in accordance with a number of embodiments of the present disclosure.

FIG. 5 is a flow diagram representing an example method 570 for data transmission in accordance with a number of embodiments of the present disclosure. The method 570 may be performed, in some examples, using a system such as devices 100 and 102, system 222, system 330 and/or system 402 as described with respect to FIGS. 1-4.

At 572, the method 570 includes detecting, at a first processing resource of a first device (e.g., a wearable device), a triggering event. The triggering event can include, for instance, a request for communication from a second processing resource, for instance, that is part of a second device (e.g., an observer device), signaling from a radio in communication with a third processing resource configured to monitor data associated with heath data of a wearer of the first device, or signaling from a radio in communication with a fourth processing resource configured to monitor data associated with a physical location of the first device, among others. Put another way, the triggering event can include a request from an observer device for information or two-way communication or signaling receive from a sensor (e.g., health data sensor, location sensor, etc.), among others. As used herein, the use of a radio can include the transmission and/or reception of information through intervening media (e.g., air, space, nonconducting materials, etc.). This can include, for instance, radio waves or other wireless communication and/or signaling including but not limited to cellular communication, one-way communication, two-way communication, radar, radiolocation, radio remote control, satellite communication, Wi-Fi, 3G, 4G, 5G, and/or other communication standards, among others.

The method 570, at 574 includes determining, at the first processing resource, an output data type associated with the triggering event, wherein the output data type is a first type for display at a second device or a second type to initiate communication between the first device and one or more second devices. For example, upon detection of the triggering event, it can be determined what associated output is warranted. For instance, in a non-limiting example, a triggering event can include receipt of a status request from a second device. For instance, a child may be curious where his or her non-English-speaking parent is after an unsuccessful attempt to the parent at the parent's home phone. The first device can receive the request, detect the request as a triggering event, and determine the output to be, for instance, either the first output data type for display at the second device or the second output data type to initiate communication between the first device and the second device (and/or additional second devices).

At 576, the method 570 includes transmitting, via a radio, the output data to a second processing resource of the second device via a device-to-device data link in response to determining the output data type comprises the first type for display at the second device. For instance, in the aforementioned example, it may be determined to transmit a display-only message indicating the parent's GPS location, and this can be transmitted via a low-latency, high-bandwidth wireless receiver, transmitter, or both. For example, the first device may include a transmitter and the second device may include a receiver.

At 578, the method 570 includes determining the output data type comprises the second type to initiate communication between the first device and one or more second devices. For instance, in the aforementioned example, it may be determined that communication may be allowed between the first device and the second device. In response to that determination, the method 570, at 580, includes initiating a two-way communication path with the second processing resource of a second device, the two-way communication path comprising a device-to-device data link or a data link with a base station or access point, and at 582, the method 570 includes transmitting, via the radio and the one-way communication path, the two-way communication path, or both, the output data to the second processing resource of the second device. Transmitting the second type to initiate communication can be done, for instance, via a low-latency, high-bandwidth wireless receiver, transmitter, or both. For instance, in the aforementioned example, the two-way communication path can be initiated, and a video call can be started between the first and the second devices such that the child can see the parent and speak to him or her in the parent's preferred language.

In some examples, the first processing resource of the first device can receive a response to the first type for display at the second device or the second type to initiate communication. For instance, in the example where the child receives a display of the parent's location, the child may respond by requesting two-way communication with the first device, which can act as a triggering event to initiate two-way communication between the first device and the second device.

Figure 6:
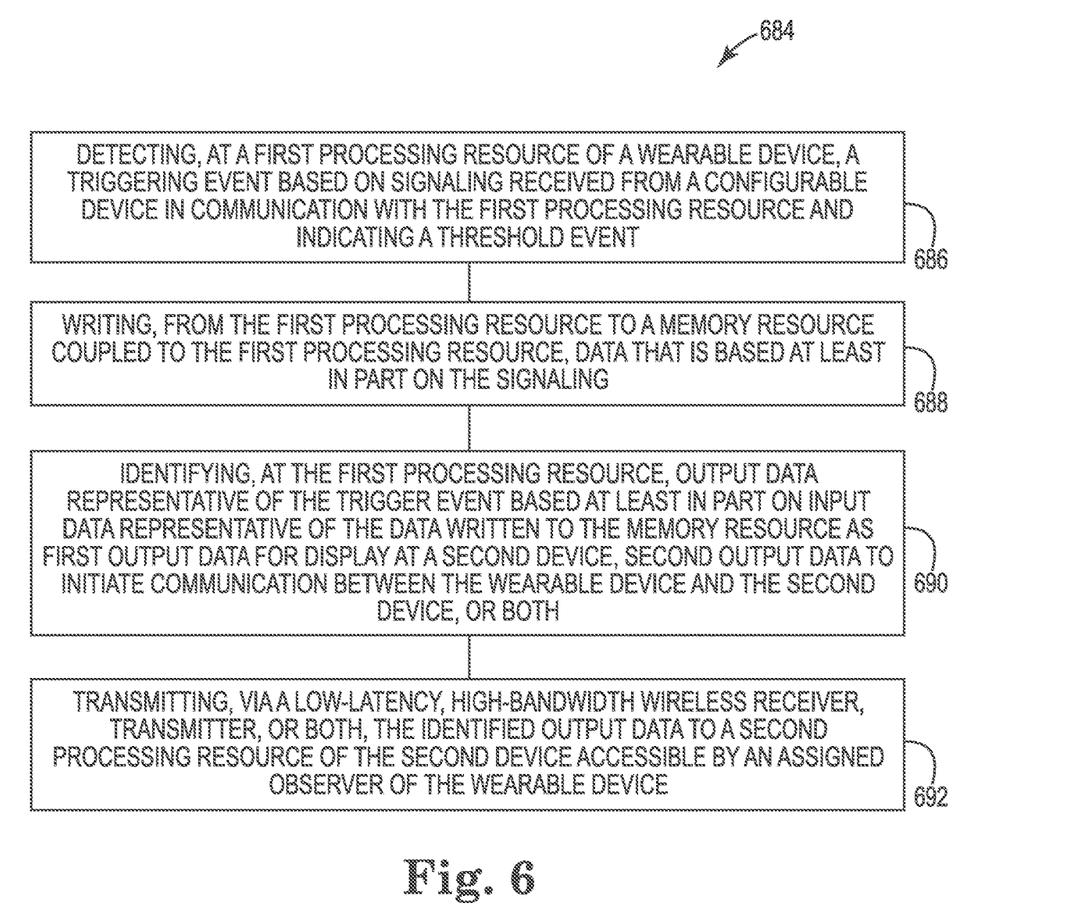
FIG. 6 is another flow diagram representing an example method for data transmission in accordance with a number of embodiments of the present disclosure.

FIG. 6 is another flow diagram representing an example method 684 for data transmission in accordance with a number of embodiments of the present disclosure. The method 684 may be performed, in some examples, using a system such as devices 100 and 102, system 222, system 330 and/or system 402 as described with respect to FIGS. 1-4.

At 686, the method 684 includes detecting, at a first processing resource of a wearable device, a triggering event based on signaling received from a configurable device in communication with the first processing resource and indicating a threshold event. For instance, the configurable device can include a sensor that has been configured to alert the first processing resource of a threshold event. The signaling, for instance, can include signaling received from a health sensor indicating a threshold health event associated with a wearer of the wearable device, signaling received from a location sensor indicating the wearable device is outside of a predetermined location radius threshold, signaling received from a temperature sensor indicating a temperature of a wearer of the wearable device outside of a threshold temperature, an ambient temperature of the wearable device outside of a threshold temperature, or both, or any combination thereof. For instance, a wearable device may be in communication with a plurality of sensors.

The method 684, at 688, includes writing, from the first processing resource to a memory resource coupled to the first processing resource, data that is based at least in part on the signaling. For instance, in the temperature sensor example, the threshold temperature or temperatures exceeded may be written to the memory resource for future tracking. For instance, this may allow a wearer of the wearable device or an observer to track the wearer's temperature spikes over time. Additionally, this information may be presented to healthcare providers upon request.

At 690, the method 684 includes identifying, at the first processing resource, output data representative of the trigger event based at least in part on input data representative of the data written to the memory resource as first output data for display at a second device, second output data to initiate communication between the wearable device and the second device, or both. For example, in the previous example, output data representative of a trigger event including the ambient temperature rising above a threshold may result in identification of the output data as a type for display at a second device. For instance, the wearable device may transmit a visual, one-way communication regarding the ambient temperature. If, in the previous example, output data representative of the trigger even includes the body temperature of the wearer rising above a threshold, the output data may be identified as a type to initiate communication between the wearable device and the second device. For instance, the wearable device may initiate a video call to the second device.

At 692, the method 684 includes transmitting, via a low-latency, high-bandwidth wireless receiver, transmitter, or both, the identified output data to a second processing resource of the second device accessible by an assigned observer of the wearable device. For instance, the wearable device may provide real-time alerts and information to the second device and vice versa. In addition, the wearable device may or may not be coupled to a different mobile device to maintain service. For instance, the wearable device can be a stand-alone device that transmits and receives data via the low-latency, high-bandwidth wireless transmitter and receiver.

Transmitting the identified output data can include, for instance, any of transmitting a message, transmitting a location of the wearable device, transmitting image data, transmitting audio data, initiating a voice call, initiating a video call, transmitting and emergency alert, or any combination thereof to the second processing resource. In some examples, the wearable device and/or associated hardware can be configured to transmit the identified output data in response to particular triggering events and to transmit the identified output data in particular manners (e.g., message vs. call, display vs. voice, etc.).

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
    receiving, at a first processing resource of a first device and from a second processing resource of a second device, a first sensor configuration determined at the second processing resource and associated with a first sensor of the first device;
    determining, at the first processing resource, a second sensor configuration associated with the first sensor of the first device, a second sensor of the first device, or both;
    detecting, at the first processing resource of the first device, a triggering event based on input received at the first sensor, the second sensor, or both, and based on the first sensor configuration, the second sensor configuration, or both;
    determining, at the first processing resource, an output data type associated with the triggering event, wherein the output data type is a first type for display at a second device or a second type to initiate communication between the first device and one or more second devices;
    in response to determining the output data type comprises the first type for display at the second device, transmitting, via a radio, the output data to a second processing resource of the second device via a device-to-device data link;
    in response to determining the output data type comprises the second type to initiate communication between the first device and one or more second devices:
        initiating a two-way communication path with the second processing resource of a second device, the two-way communication path comprising a device-to-device data link or a data link with a base station or access point; and
        transmitting, via the radio and the one-way communication path, the two-way communication path, or both, the output data to the second processing resource of the second device.

2. The method of claim 1, further comprising receiving, at the first processing resource of the first device, a response to the first type for display at the second device or the second type to initiate communication.

3. The method of claim 1, wherein transmitting the first type for display at the second device via the radio comprises transmitting the first type for display at the second device via a low-latency, high-bandwidth wireless receiver, transmitter, or both.

4. The method of claim 1, wherein transmitting the second type to initiate communication further comprises transmitting the second type to initiate communication via a low-latency, high-bandwidth wireless receiver, transmitter, or both.

5. The method of claim 1, further comprising detecting, at the first processing resource, a request for communication from the second processing resource as the triggering event.

6. The method of claim 1, further comprising:
    receiving, at the first processing resource, signaling from a radio in communication with a third processing resource configured to monitor data associated with heath data of a wearer of the first device; and
    detecting, at the first processing resource, the signaling as the triggering event.

7. The method of claim 1, further comprising:
    receiving, at the first processing resource, signaling from a radio in communication with a fourth processing resource configured to monitor data associated with a physical location of the first device; and
    detecting, at the first processing resource, the signaling as the triggering event.

8. A system, comprising:
    a wearable device in communication with a sensor and configured to:
        receive, at a first processing resource of the wearable device and from a third processing resource of a device, a sensor configuration determined at the third processing resource and associated with the sensor of the wearable device;
        detect, at the first processing resource of the wearable device, a triggering event based on input received at the sensor and based on the sensor configuration, wherein the triggering event comprises signaling received at the first processing resource from the second processing resource of the sensor;
        determine, at the first processing resource, an output data type associated with the triggering event, wherein the output data type comprises a first type for display at the device, a second type to initiate communication between the wearable device and the device, or both; and
    the device having the third processing resource in communication with the wearable device via a low-latency, high-bandwidth wireless receiver, transmitter, or both and configured to:
        receive at the third processing resource of the device, output data of the determined output data type.

9. The system of claim 8, further comprising the wearable device configured to initiate a one-way communication path, a two-way communication path, or both, with the third processing resource based on the determined output data type.

10. The system of claim 9, further comprising the wearable device configured to transmit via the one-way communication path, the two-way communication path comprising a device-to-device data link or a data link with a base station or access point, or both, the determined output data to the third processing resource of the device.

11. The system of claim 8, wherein the sensor is at least one of a temperature sensor, a location sensor, a health sensor, a motion sensor, a battery sensor, or a combination thereof.

12. The system of claim 8, wherein the sensor is configured such that the signaling received at the first processing resource is transmitted in response to a threshold event detected at the second processing resource of the sensor.

13. The system of claim 8, wherein:
    the wearable device comprises a camera, a microphone, or both and a memory resource in communication with the first processing resource; and
    the first processing resource is configured to share with the third processing resource image data, sound data, or both collected via the camera, the microphone, or both, and stored in the memory resource.

14. The system of claim 8, further comprising the first processing resource to write the first type for display at the device, the second type to initiate communication, or both, to a cloud storage service or other storage.

15. The system of claim 8, further comprising the first processing resource automatically, with limited or no additional interaction, initiating a two-way communication path with the third processing resource of the device in response to the device initiating communication with the wearable device and the second device identified as a known contact.

16. A method, comprising:
receiving, at a first processing resource of a wearable device and from a second processing resource of a second device, a configurable device configuration determined at the second processing resource and associated with a configurable device of the first device; p1 detecting, at the first processing resource of a wearable device, a triggering event based on the first configurable device configuration and based on signaling received from the configurable device in communication with the first processing resource and indicating a threshold event;
writing, from the first processing resource to a memory resource coupled to the first processing resource, data that is based at least in part on the signaling;
identifying, at the first processing resource, output data representative of the trigger event based at least in part on input data representative of the data written to the memory resource as first output data for display at the second device, second output data to initiate communication between the wearable device and the second device, or both;
transmitting, via a low-latency, high-bandwidth wireless receiver, transmitter, or both, the identified output data to the second processing resource of the second device accessible by an assigned observer of the wearable device; and
receiving, at the first processing resource, initiation of a two-way communication path from the second processing resource, wherein the two-way communication is automatically opened at the wearable device.

17. The method of claim 16, wherein the signaling received from the configurable device indicating a threshold event comprises the signaling received from a health sensor indicating a threshold health event associated with a wearer of the wearable device.

18. The method of claim 16, wherein the signaling received from the configurable device indicating a threshold event comprises the signaling received from a location sensor indicating the wearable device is outside of a predetermined location radius threshold.

19. The method of claim 16, wherein the signaling received from the configurable device indicating a threshold event comprises the signaling received from a temperature sensor indicating a temperature of a wearer of the wearable device outside of a threshold temperature, an ambient temperature of the wearable device outside of a threshold temperature, or both.

20. The method of claim 16, wherein transmitting the identified output data comprises any of transmitting a message, transmitting a location of the wearable device, transmitting image data, transmitting audio data, initiating a voice call, initiating a video call, transmitting and emergency alert, or any combination thereof to the second processing resource.

* * * * *